United States Patent
Gronau et al.

(10) Patent No.: US 8,409,127 B2
(45) Date of Patent: Apr. 2, 2013

(54) BLOOD PROCESSING DEVICE AND METHOD FOR PURGING A SET OF BLOOD LINES ON A BLOOD PROCESSING DEVICE

(75) Inventors: Soeren Gronau, Nauheim (DE); Juergen Haecker, Neu-Anspach (DE); Goetz Guenther, Bad Homburg (DE); Max Fischer, Frankfurt am Main (DE); Joachim Noack, Bad Neustadt (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 783 days.

(21) Appl. No.: 12/310,115

(22) PCT Filed: Aug. 27, 2007

(86) PCT No.: PCT/EP2007/007505
§ 371 (c)(1), (2), (4) Date: Dec. 9, 2009

(87) PCT Pub. No.: WO2008/028579
PCT Pub. Date: Mar. 13, 2008

(65) Prior Publication Data
US 2010/0087772 A1   Apr. 8, 2010

(30) Foreign Application Priority Data
Sep. 7, 2006   (DE) .......................... 10 2006 042 120

(51) Int. Cl.
*A61M 5/00* (2006.01)
(52) U.S. Cl. ...................................... 604/6.09; 604/6.11
(58) Field of Classification Search ........ 604/4.01–6.07, 604/6.09–6.16; 210/85, 134, 143, 252, 258, 210/645, 646
See application file for complete search history.

(56) References Cited

U.S. PATENT DOCUMENTS

| | | | | |
|---|---|---|---|---|
| 5,368,555 A | * | 11/1994 | Sussman et al. | 604/6.05 |
| 5,685,835 A | | 11/1997 | Brugger | |
| 5,932,103 A | * | 8/1999 | Kenley et al. | 210/646 |
| 5,948,251 A | | 9/1999 | Brugger | |

FOREIGN PATENT DOCUMENTS

| | | |
|---|---|---|
| DE | 32 42 744 A1 | 6/1986 |
| DE | 102 45 619 A1 | 3/2004 |
| DE | 696 32 045 T2 | 11/2004 |
| EP | 0 578 175 A1 | 1/1994 |
| EP | 0 830 153 B1 | 3/2004 |
| EP | 1 161 271 B1 | 8/2005 |
| WO | WO 96/40313 | 12/1996 |
| WO | WO 01/51106 A1 | 7/2001 |

\* cited by examiner

Primary Examiner — Philip R Wiest
(74) Attorney, Agent, or Firm — Jacobson Holman PLLC

(57) ABSTRACT

A method for emptying a blood tubing set of a blood treatment device that includes an extracorporeal blood circuit with a membrane filter includes supplying air or gas to the blood tubing set to displace liquid therein. The blood tubing set includes arterial and venous patient blood tubes in communication with a first chamber of the membrane filter. The device also includes a substituate line which opens into the arterial blood tube and/or into the venous blood tube, and a substituate pump. To empty the blood tubing set, the arterial blood tube and the venous blood tube are connected to one another to provide a circuit that includes the membrane filter, the arterial blood tube, and the venous blood tube. The substituate line is disconnected, and the air or gas is pumped into the blood tubing set so as to displace liquid into a second chamber of the membrane filter.

15 Claims, 1 Drawing Sheet

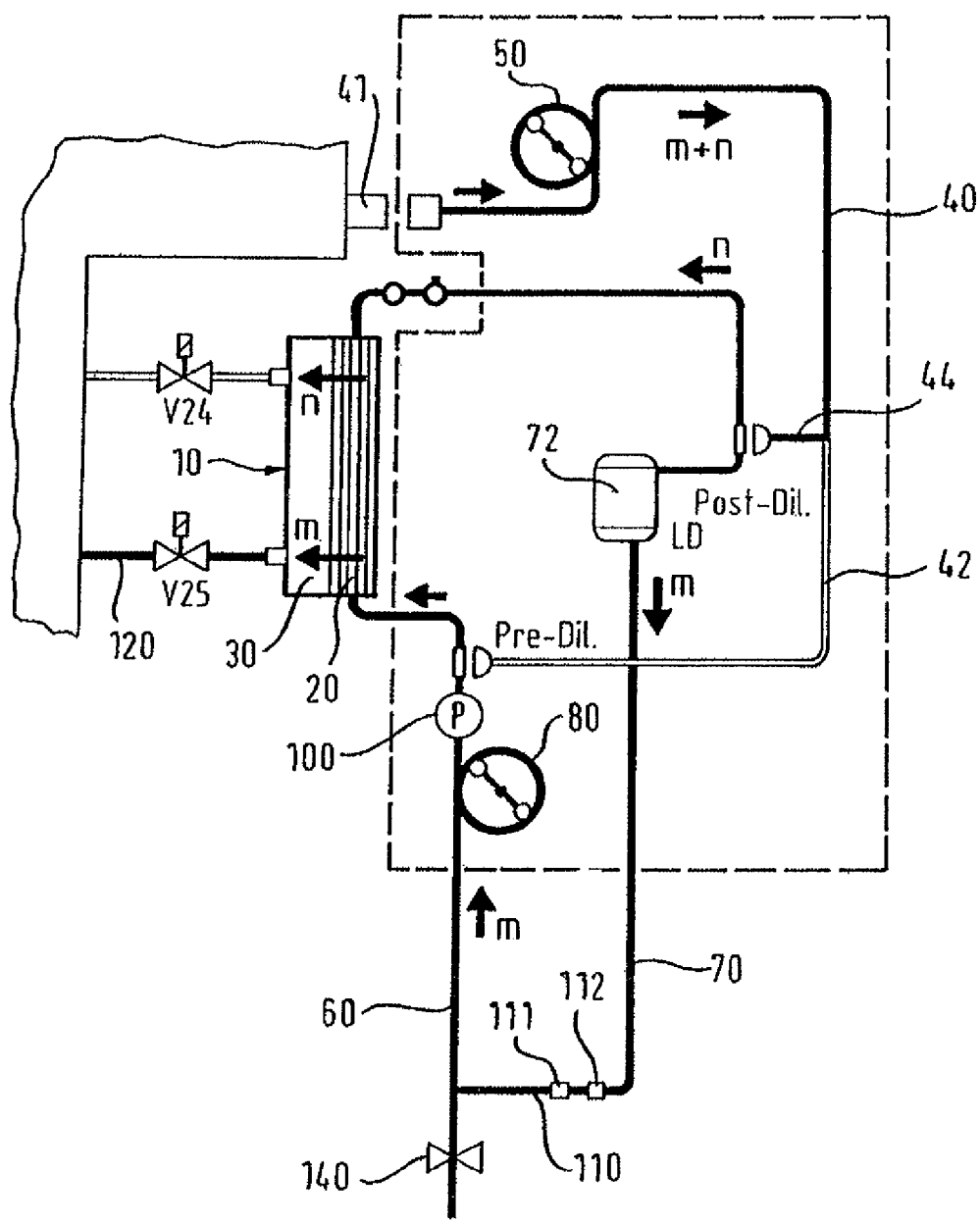

BLOOD PROCESSING DEVICE AND METHOD FOR PURGING A SET OF BLOOD LINES ON A BLOOD PROCESSING DEVICE

CROSS-REFERENCE TO RELATED APPLICATION

This is a national stage of PCT/EP07/007505 filed Aug. 27, 2007 and published in German, which has a priority of Germany no. 10 2006 042 120.5 filed Sep. 7, 2006, hereby incorporated by reference.

BACKGROUND OF THE INVENTION

1. Field of Invention

The invention relates to a method for the emptying of a blood tubing set of a blood treatment device for extracorporeal blood treatment comprising a membrane filter having a first chamber, namely a blood chamber, and a second chamber separated therefrom by a membrane, said first chamber being flowed through by blood in operation of the blood treatment device and said second chamber being flowed through by filtrate in operation of the blood treatment device, and said blood tubing set including an arterial blood tube and a venous blood tube which are both in communication with the first chamber of the membrane filter and which conduct blood from the patient to the membrane filter and from the membrane filter to the patient in operation of the blood treatment device, and comprising a substituate line which opens into the arterial blood tube and/or into the venous blood tube, and comprising a substituate pump which is in communication with the substituate line such that it conveys substituate from a substituate source through the substituate line. The named membrane filter can, for example, be a hemodiafilter or a hemofilter.

2. Description of the Prior Art

Different methods for the emptying of a blood tubing set are known from the prior art. It is known from EP 1 161 271 A1 to operate dialysate pumps located on the dialysate side for the purpose of emptying the blood tubing set such that a pressure drop is adopted over the membrane of the dialyzer by means of which the liquid located in the blood tubing set is transported via the membrane of the dialyzer to the dialysate side, that is into the second chamber, and is removed from there by means of draining lines. A substituate bag is in communication with the blood tubing set and collapses due to the emptying of the blood tubing set or due to the low pressure located therein. As soon as the pressure in the blood tubing set falls below a specific threshold, a valve is opened via which air is sucked into the blood treatment tubing set until the pressure in the blood tubing set corresponds to atmospheric pressure.

The blood pump is in operation during the emptying of the blood tubing set via the membrane of the dialyzer until the liquid has been removed from the blood tubing set.

It is known from EP 0 830 153 A1 to displace liquid from the blood tubing set and also from the dialysate circuit by means of air before the corresponding hose lines are separated from the dialyzer.

Finally, DE 34 42 744 A1 discloses a method in which the liquid in the blood tubing set is displaced with the help of a ring line in the blood tubing set and with the help of an air source. The subject of the patent application is to be able to carry out a leak test or a pressure test on the dialyzer.

SUMMARY OF THE INVENTION

It is the underlying object of the present invention to remove the mixture of blood and displacement means or substituate from the blood tubing set in a simple and efficient manner at the end of the returning of blood to the patient or at the end of the blood treatment.

This object is solved by a method having the features described herein. Provision is accordingly made for the arterial blood tube and the venous blood tube to be connected to one another for the purpose of the emptying of the blood tubing set such that a circuit is created which includes the blood chamber, the arterial blood tube and the venous blood tube, for the substituate line to be disconnected from the substituate source, and for air to be pumped into the blood tubing set by means of the substituate pump such that excess pressure arises in the blood tubing set by which the liquid is displaced from the blood chamber into the second chamber of the membrane filter via the membrane.

It is thus the subject of the invention that the substituate pump anyway present is utilized to convey air into the blood tubing set for the purpose of emptying the blood tubing set, whereupon the mixture of blood and substituate or displacement means is displaced from the blood chamber into the second chamber of the membrane filter via the membrane and is conducted away from said second chamber via draining lines. It is possible in this manner to effect an efficient displacement of liquid from the blood tubing set with a comparatively low effort.

The method in accordance with the invention takes place without the involvement of the patient, i.e. at the end of the patient treatment with a disconnected patient.

As soon as the emptying method in accordance with the invention has ended, the blood tubing set, which is typically a disposable article, can be disposed of. Waste disposal costs due to the lower waste mass can be reduced by the emptying of the blood tubing set. Furthermore, hygienic reasons speak for a complete emptying of the blood tubing set before its disposal.

The blood treatment device has a control for the carrying out of the method in accordance with the invention. It can be a control device in addition to the control device of the blood treatment device anyway present. It is also conceivable that the named control is realized in the control device anyway present for the operation of the blood treatment device, with this control device preferably being expanded in this case such that it carries out the control of the substituate pump and/or of the pressure sensor and/or of possible valves in the arterial blood tube or the venous blood tube or branch and/or such that the air entry into the substituate line of the blood tubing set is made possible automatically. These extensions can be realized, for example, by a software change.

It must be pointed out in this connection that the disconnection of the substituate line from the substituate source preferably takes place manually by the treatment staff. It is, however, also conceivable to automate an opening with respect to ambient air and to perform it via the control. Within the framework of the present invention, not only the physical separation, i.e. the uncoupling, of the substituate line from the substituate source is to be understood under the term "disconnection", but e.g. also the closing of the line between the substituate pump and the substituate source.

Provision is made in a further embodiment of the invention for the substituate pump to be loaded with ambient air which is then conveyed into the blood tubing set by the substituate pump.

The substituate line can be made as a predilution line and/or as a post-dilution line. Lines of this type are utilized to dilute the blood before the entry into the blood chamber (predilution) or after the discharge from the blood chamber (post-dilution) during the operation of the blood treatment device. A combined process of predilution and post-dilution is also conceivable.

The substitute line in this embodiment of the invention can branch into a predilution line and into a post-dilution line which opens into the arterial blood tube before the membrane filter, on the one hand, and which opens into the venous blood tube after the membrane filter, on the other hand.

Provision is preferably made for one of the two lines (pre-dilution line, post-dilution line) to be shut off on the emptying of the blood tubing set so that the air compressed in the substitute pump is only conveyed into the blood tubing set through the other of these lines.

It is, for example, conceivable that both the predilution line and the post-dilution line are provided with shut-off valves by means of which their lines can be closed. It is, for example, conceivable that the valve of the predilution line is closed and the air compressed by the substitute pump is thus only conveyed into the blood tubing set via the post-dilution line.

Provision is made in a further aspect of the invention for a blood pump to be arranged such that it is in communication with one of the blood tubes, preferably with the arterial blood tube, such that blood is conveyed through the blood tubing set in the operation of the blood treatment device, with the blood pump being in operation at least at times during emptying of the blood tubing set. The blood pump can thus engage in a supporting manner on the emptying of the blood tubing set.

Provision is made in a further aspect of the invention for the air conveyed by means of the substitute pump to be conveyed into the arterial blood tube or into the venous blood tube via the predilution line or the posit-dilution line and for it to be split in this such that the air or the liquid displaced by the air enters into the blood chamber both via the arterial blood tube and via the venous blood tube. It is, for example, possible for the air to be introduced via the post-dilution line into the venous blood tube and to be split there. One part of the air enters into the blood chamber from one side against the usual flow direction in operation of the blood treatment device, and the other part of the air enters into the blood chamber from the other side through the arterial line via the short-circuit between the arterial blood tube and the venous blood tube. In this manner, a complete emptying of the blood tubing set is possible with comparatively simple means.

In accordance with a further aspect of the invention, provision can be made for the substitute pump to be switched off again after a predetermined time period after the switch-on time. It is thus possible for the substitute pump to stop and for the blood tubing set to be considered empty after a defined time period.

It is likewise conceivable for a pressure sensor to be provided which is arranged such that it measures the pressure in the arterial blood tube and/or in the venous blood tube and for a control device to be provided to which the pressure sensor is connected and which switches the substitute pump off as soon as the pressure detected by means of the pressure sensor exceeds a threshold. A wet membrane is substantially more permeable for liquid than for air and, at the point in time of the complete emptying, a significant pressure increase can thus be measured which is used in this embodiment of the invention to switch off the substitute pump because the blood tubing set is identified as empty.

In a further aspect of the invention, it is possible for a line section to branch off from the arterial blood tube and/or from the venous blood tube and for this line section to be connected to the arterial blood tube or the venous blood tube or to a further line section arranged thereon to establish the circuit. Provision is further made for the arterial blood tube and/or the venous blood tube to be shut off downstream of the junction of the branching off line section to prevent liquid from being discharged from the arterial blood tube or the venous blood tube.

The invention furthermore relates to a blood treatment device having an extracorporeal blood circuit which is suitable for the reception of a blood tubing set as well as of a membrane filter comprising a first chamber and a second chamber separated therefrom by a membrane, said first chamber being flowed through by blood in operation of the blood treatment device and said second chamber being flowed through by filtrate in operation of the blood treatment device. The blood treatment device is characterized in that it has a substitute pump and a control unit which controls the substitute pump for the emptying of the blood tubing set such that air or gas is pumped into the blood tubing set by means of the substitute pump so that excess pressure is created in the blood tubing set by which liquid is displaced from the first chamber into the second chamber of the membrane filter via the membrane.

Provision is made in a preferred embodiment of the invention for the substitute pump to be made such that is sucks in ambient air and conveys it into the blood tubing set after the disconnection of the substitute line.

In a further aspect of the invention, a blood pump is provided which is controlled on the part of the control unit for the purpose of emptying the blood tubing set such that it is in operation permanently or from time to time during the emptying of the blood tubing set.

In a further aspect of the invention, the control unit is made such that it switches off the substitute pump again after a predetermined time period after the switch-on time. The possibility thus exists of the control unit stopping the substitute pump at the end of a defined time period and of the blood tubing set then being considered empty.

In a further aspect of the invention, a pressure sensor is provided which is connected to the control unit and which is arranged such that it measures the pressure in the arterial blood tube and/or in the venous blood tube. Provision is made in this case for the substitute pump to be switched off by the control device as soon as the pressure detected by means of the pressure sensor exceeds a threshold.

BRIEF DESCRIPTION OF THE DRAWINGS

Further details and advantages of the invention will be explained in more detail with reference to an embodiment shown in the drawing. The only FIGURE shows a schematic representation of a blood treatment method for the example of a hemodiafiltration method.

DETAILED DESCRIPTION OF THE PREFERRED EMBODIMENTS

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

The blood treatment device has a filtrate side and an extracorporeal blood circuit. The extracorporeal blood circuit comprises a blood tubing set as well as the first chamber 20 of the membrane filter 10 which is separated from the second chamber 30 by a semipermeable membrane. In the operation of the device, blood is taken from the patient via the arterial blood tube 60, is introduced into the first chamber 20 and is then led back to the patient again via the venous blood tube 70 and the drip chamber 72 located thereon. The conveying of the blood in the extracorporeal circuit takes place via the blood pump 80 which is arranged in the arterial blood tube 60. The dashed line in the FIGURE characterizes the part of the assembly made as disposable.

As can further be seen from the FIGURE, a substitute pump 50 is provided which is located in the substitute line 40. The substitute line has a connector via which the substituate line 40 is connected to a substitute source. The substituate in this embodiment is prepared online in the blood treatment device and made available at the substitute port 41. It is generally likewise feasible to provide a substitute source independently of the blood treatment machine.

In operation, the substitute pump 50 conveys substitute through the substitute line 40. The substitute line 40 opens into the blood tubing set via a predilution line 42 and a post-dilution line 44. Provision is made in detail for the predilution line 42 to open into the arterial blood tube 60 and for the post-dilution line 44 to open into the venous blood tube 70. As can be seen from the FIGURE, the predilution line 42 opens into a line section between the blood pump 80 and the first chamber of the membrane filter 10. The post-dilution line 44 opens into a line section between the membrane filter 10 and the venous drip chamber 72.

For the purpose of the emptying of the blood tubing set including the hoses 60 and 70, the substitute line 40 is now separated from the connector port 41 of the substitute source by the treatment staff, preferably manually. Furthermore, the line section 110 branching off from the arterial blood tube 60 is short-circuited via connectors 111, 112 with the venous blood tube 70 by the treatment staff, likewise preferably manually, so that a circuit arises which includes the arterial blood tube 60, the venous blood tube 70, the venous drip chamber 72 and the first chamber 20 of the membrane filter 10. The section of the arterial blood tube 60 which does not belong to the circuit and which is located below the junction of the line 110 branching off is closed by a shut-off element 140.

The substitute pump 50 now conveys air into the substituate line 40, as is characterized by the arrow and the marking "m+n", corresponding to the disconnection of the substituate line from the substitute source. During this, the predilution line 42 is connected via a suitable valve. The total airflow conveyed through the substitute pump 50 is thus conveyed into the venous blood tube 70 via the post-dilution line 44. It splits here into the part flows "n" and "m", with the part flow "n" or the liquid displaced thereby entering into the first chamber 20 of the membrane filter 10 from above via the outlet stub in accordance with the FIGURE against the flow direction customary during the operation of the blood treatment device. The other part of the air supplied, which is marked by "m" in the FIGURE or the liquid displaced thereby is guided via the venous drip chamber 72 and enters via the connectors 111, 112 and the line section 110 into the arterial blood hose 60 and via the latter via the inlet port of the first chamber into the first chamber 20 of the membrane filter 10.

The first chamber 20 of the membrane filter 10 is thus loaded at both sides with air/liquid and thus with pressure so that the liquid contained in the blood tube set or the liquid/air mixture is transported from the first chamber 20 via the semipermeable chamber into the second chamber 30 of the membrane filter 10 and is then drained off by means of the line 120.

During this emptying procedure, the blood pump 80 located in the arterial blood tube 60 can run permanently or at least at times for the support of the emptying process. The pressure sensor 100, which measures the pressure in the arterial blood tube 60 during the emptying process, is located downstream of the blood pump 80 in the arterial blood tube 60. If the pressure value measured is below a threshold value, it is found that the blood tubing set is empty and the pumps 50, 80 are switched off.

Alternatively to this, there is the possibility of ending the emptying process at the end of a predetermined time period after the start of the process.

The method in accordance with the invention provides a simple and efficient possibility of emptying a blood tubing set by which the waste weight is reduced and hygiene is improved. The method in accordance with the invention preferably runs automatically, that is intervention by the user is preferably not required, with the exception of the disconnection of the substitute line from the substitute connector port and the short-circuiting of the connectors 111, 112 (which preferably take place manually).

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

What is claimed is:

1. A method for emptying a blood tubing set of a blood treatment device that includes an extracorporeal blood circuit with a membrane filter having a first chamber and a second chamber separated therefrom by a membrane, said first chamber conveying blood in operation of the blood treatment device and said second chamber conveying filtrate in operation of the blood treatment device, and said blood tubing set including an arterial blood tube and a venous blood tube which are both in communication with the first chamber of the membrane filter and which conduct the blood from a patient to the membrane filter and from the membrane filter to the patient in operation of the blood treatment device, and including a substitute line which opens into at least one of the arterial blood tube and the venous blood tube, and a substituate pump which is in communication with the substitute line to convey substitute from a substitute source through the substitute line, said method comprising:
    connecting the arterial blood tube and the venous blood tube to one another to provide a circuit that includes the membrane filter, the arterial blood tube, and the venous blood tube;
    disconnecting the substitute line from the substitute source; and
    pumping air or gas into the blood tubing set with the substituate pump to provide an excess pressure in the blood tubing set by which liquid is displaced, via the membrane, into the second chamber of the membrane filter.

2. The method in accordance with claim 1, wherein the substitute pump is loaded with ambient air which is conveyed into the blood tubing set through the substitute pump.

3. The method in accordance with claim 1, wherein the substitute line is configured as at least one of a predilution line and a post-dilution line.

4. The method in accordance with claim 1, wherein the substitute line branches into a predilution line and into a post-dilution line; and wherein, on the emptying of the blood tubing set, the predilution line or the post-dilution line is shut off so that the air compressed in the substitute pump is only transported into the blood tubing set through the predilution line or the post dilution line.

5. The method in accordance with claim 1, wherein a blood pump is arranged which is in communication with one of the blood tubes such that, in the operation of the blood treatment device, blood is conveyed through the blood tubing set; and wherein the blood pump is in operation permanently or periodically during the emptying of the blood tubing set.

6. The method according to claim 5, wherein the blood pump is in communication with the arterial blood tube.

7. The method in accordance with claim 1, wherein the air conveyed with the substituate pump is conveyed via the pre-dilution line or the post-dilution line into the arterial blood tube or the venous blood tube, and is split in the venous blood tube such that the air or the liquid displaced by the air enters into the first chamber of the membrane filter both via the arterial blood tube and via the venous blood tube.

8. The method in accordance with claim 1, wherein the substituate pump is switched off after a predetermined time period after a switch-on time.

9. The method in accordance with claim 1, wherein a pressure sensor is provided which is arranged to measure pressure in at least one of the arterial blood tube and the venous blood tube; and wherein a control device is provided to which the pressure sensor is connected and which switches the substituate pump off as soon as the pressure detected by the pressure sensor exceeds a threshold.

10. The method in accordance with claim 1, wherein a line section branches off from at least one of the arterial blood tube and the venous blood tube; wherein the line section is connected to the arterial blood tube or to the venous blood tube or to a line section arranged thereon; and wherein at least one of the arterial blood tube and the venous blood tube is shut off downstream of the junction of the branching off line section.

11. A blood treatment device that includes an extracorporeal circuit configured for receiving a blood tubing set and a membrane filter, said membrane filter having a first chamber and a second chamber separated therefrom by a membrane, said first chamber conveying blood in operation of the blood treatment device and said second chamber conveying filtrate in operation of the blood treatment device, said blood treatment device comprising:
a substituate pump connected to a substituate line which opens into the blood tubing set and a control unit which controls the substituate pump configured to empty the blood tubing set by pumping air or gas into the blood tubing set with the substituate pump to provide excess pressure in the blood tubing set by which liquid is displaced, via the membrane, from the first chamber into the second chamber of the membrane filter.

12. The blood treatment device in accordance with claim 11, wherein the substituate pump takes in ambient air through a substituate line and conveys the air into the blood tubing set after disconnection of the substituate line from a substituate source.

13. The blood treatment device in accordance with claim 11, further comprising a blood pump; and wherein the control unit is configured to control the blood pump for the emptying of the blood tubing set such that the blood pump is in operation permanently or periodically during the emptying of the blood tubing set.

14. The blood treatment device in accordance with claim 11, wherein the control unit switches the substituate pump off after a predetermined time period from a switch-on time.

15. The blood treatment device in accordance with claim 11, further comprising a pressure sensor which is connected to the control unit and which measures a pressure in at least one of an arterial blood tube and a venous blood tube; and wherein the control unit switches off the substituate pump as soon as the pressure detected by the pressure sensor exceeds a threshold.

* * * * *

UNITED STATES PATENT AND TRADEMARK OFFICE
CERTIFICATE OF CORRECTION

PATENT NO. : 8,409,127 B2
APPLICATION NO. : 12/310115
DATED : April 2, 2013
INVENTOR(S) : Gronau et al.

It is certified that error appears in the above-identified patent and that said Letters Patent is hereby corrected as shown below:

On the title page, column 1, section (86), change:

"§ 371 (c)(1),
  (2), (4) Date: Dec. 9, 2009"

to

--§ 371 (c)(1),
  (2), (4) Date: Dec. 8, 2009--

Signed and Sealed this
Twelfth Day of November, 2013

Teresa Stanek Rea
*Deputy Director of the United States Patent and Trademark Office*

UNITED STATES PATENT AND TRADEMARK OFFICE
CERTIFICATE OF CORRECTION

PATENT NO. : 8,409,127 B2
APPLICATION NO. : 12/310115
DATED : April 2, 2013
INVENTOR(S) : Gronau et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1060 days.

Signed and Sealed this
First Day of September, 2015

Michelle K. Lee
*Director of the United States Patent and Trademark Office*